(12) United States Patent
Kitamura et al.

(10) Patent No.: US 7,253,300 B2
(45) Date of Patent: Aug. 7, 2007

(54) PRODUCTION PROCESS FOR HIGH PURITY TRICYCLO-[5.2.1.0$^{2,6}$]DECANE-2-CARBOXYLIC ACID ESTER

(75) Inventors: Mitsuharu Kitamura, Okayama (JP); Takashi Kojima, Ibaraki (JP); Yoshiharu Ataka, Wakayama (JP); Tomoaki Kubota, Okayama (JP); Kinji Kato, Okayama (JP); Kazuyuki Fukuda, Tokyo (JP)

(73) Assignees: Mitsubishi Gas Chemical Company, Inc., Tokyo (JP); Kao Corporation, Tokyo (JP)

( * ) Notice: Subject to any disclaimer, the term of this patent is extended or adjusted under 35 U.S.C. 154(b) by 0 days.

(21) Appl. No.: 10/942,880

(22) Filed: Sep. 17, 2004

(65) Prior Publication Data

US 2005/0101799 A1    May 12, 2005

(30) Foreign Application Priority Data

Sep. 19, 2003   (JP)   ............................. 2003-327577
Sep. 19, 2003   (JP)   ............................. 2003-327579
Sep. 19, 2003   (JP)   ............................. 2003-327580

(51) Int. Cl.
C07C 67/36    (2006.01)
C07C 69/74    (2006.01)

(52) U.S. Cl. ................. 560/117; 560/114; 560/122; 560/116

(58) Field of Classification Search ............... 562/497, 562/498, 499; 560/114, 116, 117
See application file for complete search history.

(56) References Cited

U.S. PATENT DOCUMENTS 3,014,062 A  * 12/1961  Moller et al. ............... 560/114
4,411,828 A    10/1983  Fujikura et al.
4,973,740 A  * 11/1990  Ishihara et al. ............. 560/114

FOREIGN PATENT DOCUMENTS

| EP | 0 363 218 A2 |   | 4/1990 |
| JP | 9-194433     |   | 7/1997 |
| JP | 3436838      | * | 8/2003 |

OTHER PUBLICATIONS

European Search Report, for Application No. EP 04 10 4426, dated Feb. 15, 2005.

* cited by examiner

*Primary Examiner*—Karl Puttlitz
(74) *Attorney, Agent, or Firm*—Antonelli, Terry, Stout & Kraus, LLP.

(57) ABSTRACT

In a process for producing tricyclo[5.2.1.0$^{2,6}$]decane-2-carboxylic acid ester by reacting tricyclo[5.2.1.0$^{2,6}$]deca-3-ene with carbon monoxide and alcohol in the presence of HF, carried out separately are (a) a step in which tricyclo[5.2.1.0$^{2,6}$]deca-3-ene is reacted with carbon monoxide to produce acyl fluoride and (b) a step in which acyl fluoride obtained in the step described above is reacted with alcohol to produce an ester. Also, the reaction conditions at the step (a) described above are selected or a step for carrying out isomerization reaction of tricyclo[5.2.1.0$^{2,6}$]decane-2-carboxylic fluoride obtained at the step (a) is interposed between the step (a) and the step (b). Further, the crude product of tricyclo[5.2.1.0$^{2,6}$]decane-2-carboxylic acid ester thus obtained is subjected to contact treatment with specific glycol in the presence of an acid catalyst and then distilled.

14 Claims, No Drawings

PRODUCTION PROCESS FOR HIGH PURITY TRICYCLO-[5.2.1.0$^{2,6}$]DECANE-2-CARBOXYLIC ACID ESTER

BACKGROUND OF THE INVENTION

The present invention relates to a process for efficiently producing high purity tricyclo[5.2.1.0$^{2,6}$]decane-2-carboxylic acid ester which has a small content of impurity esters having an unsaturated bond and which has an excellent fragrance and is useful as a perfume or a perfume component.

RELATED ART

Known as a process for producing carboxylic acid esters from monoolefins is a process in which olefins are carbonylated with carbon monoxide in a strong acid by Koch reaction and in which carboxylic acid thus obtained is esterified in an acid catalyst.

In producing tricyclo[5.2.1.0$^{2,6}$]decane-2-carboxylic acid ester (hereinafter referred to as TCDCE), usually adopted is a process in which tricyclo[5.2.1.0$^{2,6}$]deca-3-ene (dihydrodicyclopentadiene, hereinafter referred to as DHDCPD) obtained by hydrogenating dicyclopentadiene (hereinafter referred to as DCPD) is reacted with carbon monoxide and water in a strong acid such as sulfuric acid to prepare tricyclo[5.2.1.0$^{2,6}$]decane-2-carboxylic acid (hereinafter referred to as TCDC) and in which this is esterified.

However, cycloolefins are liable to be polymerized in carbonylation reaction, and therefore TCDC can not be obtained at a high yield. Thus, disclosed as a process for obtaining TCDC at a high yield is a method in which reaction is carried out while bringing tricyclo[5.2.1.0$^{2,6}$]deca-8-yl formate obtained by reacting DCPD with formic acid and then hydrogenating into contact with an inorganic strong acid catalyst (refer to, for example, Japanese Patent Publication No. 40658/1986). However, in the above synthetic process for carboxylic acid, a large amount of a strong acid such as sulfuric acid and HF is consumed, so that it is not necessarily economical.

Next, esterification has to be carried out in order to use TCDC for a perfume. In general, it is difficult to esterify tertiary carboxylic acids, and particularly in the case of TCDC, a steric hindrance thereof exerts a large effect. Accordingly, disclosed is a process in which acid halide is derived from TCDC and in which it is then reacted with alcohol for esterification (refer to, for example, Japanese Patent Publication No. 1014/1986). In the above process, however, a large amount of an expensive halogenating agent is used, so that it is not necessarily an economical process. Further, TCDC is reacted with dialkyl sulfate as an esterifying agent to carry out esterification (refer to, for example, Japanese Patent Publication No. 1014/1986 and Japanese Patent Publication No. 53499/1987). However, not only dialkyl sulfate is expensive, but also the problem that it is decomposed by water formed by the reaction is involved therein.

Disclosed as a method for solving the above problems is a method in which DHDCPD is reacted with carbon monoxide and alcohol in HF through a route shown in the following scheme to cause carbonylation reaction and esterification reaction at the same time to thereby obtain TCDCE at a high yield (refer to, for example, Japanese Patent No. 2,680069):

Scheme 1

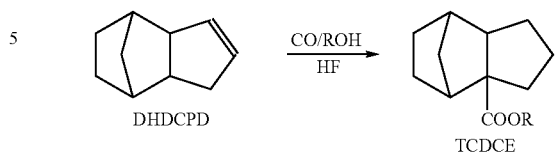

In the above method, an ester can be obtained in situ without separating carboxylic acid, and it is easy to recover an HF catalyst, so that it is a promising method in industrially carrying out. However, further detailed investigations carried out by the present inventors have shown that a small amount of an unsaturated ester is mixed as an impurity in an ester obtained by the above method. The above unsaturated ester can be converted to the product ester by hydrogenation by a conventional method, and the molecular weight thereof is smaller by 2 than that of the product ester. Accordingly, it is a compound having one double bond in an alicyclic group of TCDCE (hereinafter referred to as an unsaturated compound). This has a boiling point close to that of TCDCE, and it is difficult to separate by distillation. Further, it lowers a product value of a perfume as the product. In order to use TCDCE as a perfume, it is desired to reduce the above unsaturated compound to 1 mass % or less. It can be reduced substantially to zero by secondarily subjecting the product obtained to hydrogenation treatment, but in this case, involved therein is the problem that a hydrogenating step is separately required in order to remove a trace amount of an impurity.

As shown in the following scheme 2, present in the above TCDCE are the structural isomers of exo-tricyclo[5.2.1.0$^{2,6}$]decane-endo-2-carboxylic acid ester/endo-tricyclo[5.2.1.0$^{2,6}$]decane-exo-2-carboxylic acid ester, and they have a little different odors respectively (paying attentions to an ester group, hereinafter exo-tricyclo[5.2.1.0$^{2,6}$]decane-endo-2-carboxylic acid ester shall be referred to as an Endo isomer, and endo-tricyclo[5.2.1.0$^{2,6}$]decane-exo-2-carboxylic acid ester shall be referred to as an Exo isomer):

Scheme 2

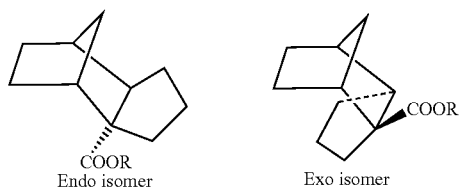

It is described in Japanese Patent Publication No. 1014/1986 that the Endo isomer of TCDCE has citrus, fruity and woody (Citrus-Fruity-Woody) odors and that the Exo isomer thereof has fresh woody and earthy (Fresh-Woody-Earthy) odors and an ethyl ester body has the most strong odor and is preferred.

When TCDCE is used as a perfume, a ratio of the Endo isomer/the Exo isomer is particularly desired to be 1.0 or more. However, in respect to a method for controlling the above isomer ratio, it is only described in the document that they can be separated by precise distillation, and no knowledge is disclosed regarding a controlling method by reaction conditions. A method for separating a mixture of the above esters by precise distillation is not necessarily an economical method as long as unnecessary fractions are not effectively utilized.

Further, it is disclosed that a content of exo-tricyclo[5.2.1.0$^{2,6}$]decane-endo-2-carboxylic acid ester can be raised by controlling an isomer ratio in DHDCPD of the raw material in terms of an exo-DHDCPD/endo-DHDCPD ratio to 8/92 or more without controlling the reaction conditions (refer to, for example, Japanese Patent Publication No. 194433/1997). However, DCPD having a high exo content has to be obtained in order to obtain the above DHDCPD, but DCPD which is usually obtainable has an Exo isomer/Endo isomer ratio of 0.5/99.5 at most, and it is difficult to obtain DCPD having a high exo content.

Accordingly, an effective method for controlling a structural isomer by reaction conditions has been desired.

It has been found by researches carried out by the present inventors that a reaction temperature of a low temperature of −10° C. or lower and the reaction condition of 15 times or more in terms of a mole ratio of HF/DHDCPD are required in order to obtain an isomer ratio of 1.0 or more in terms of an Exo isomer/Endo isomer ratio in the method described in Patent No. 2,680069 described above. However, the reaction yield is reduced on the above conditions, and the productivity is notably reduced since a large amount of HF is used as a catalyst. Accordingly, it has been found that it is a method which is difficult to industrially carry out.

Further, it has been found that a trace amount of an impurity other than the intended product is mixed in a TCDE crude product obtained by reacting DHDCPD with carbon monoxide and ethanol in HF. A trace amount of the above impurity is identified as an aldehyde compound (hereinafter referred to as impurity aldehyde) having a tricyclo[5.2.1.0$^{2,6}$]decane skeleton from a molecular weight which is smaller by 16 than that of TCDC and a fragment pattern in mass analysis.

In using TCDE as a perfume, it is desired that a content of the above impurity aldehyde is controlled to 0.5 mass % or less since the fragrance of the above impurity aldehyde exerts an adverse effect. However, since the above impurity aldehyde has a boiling point very close to that of TCDE which is the intended product, when trying to separate it by distillation, the distillation has to be carried out using a distilling column having a high separating efficiency and applying a high reflux ratio, and therefore there has been the problem that the yield at a refining step and the productivity are not avoided from being reduced.

DISCLOSURE OF THE INVENTION

Under such circumstances, an object of the present invention is to provide a process for efficiently producing high purity tricyclo[5.2.1.0$^{2,6}$]decane-2-carboxylic acid ester which has a small content of an impurity ester (unsaturated compound) having an unsaturated bond and which has an excellent fragrance and is useful as a perfume or a perfume component.

Also, an object of the present invention is to provide a process for efficiently and industrially advantageously producing high purity tricyclo[5.2.1.0$^{2,6}$]decane-2-carboxylic acid ester in which an Endo isomer/Exo isomer ratio is 1.0 or more and which has an excellent fragrance and is useful as a perfume or a perfume component.

Further, an object of the present invention is to provide a process for effectively removing a trace amount of impurity aldehyde from a TCDE crude product to industrially advantageously produce high purity tricyclo[5.2.1.0$^{2,6}$]decane-2-carboxylic acid ester which is suited as a perfume or a perfume component.

The present inventors have intensively investigated a method for inhibiting formation of an impurity ester having an unsaturated bond in a process for producing TCDCE from DHDCPD, carbon monoxide and alcohol using an HF catalyst. As a result thereof, it has been clarified by them that an acid strength of HF is reduced due to esters formed in a system at a latter half of the reaction and unreacted alcohol in a process in which carbonylation and esterification are caused at the same time as is the case with the process described in Patent No. 2,680069 described above, whereby a carbonylation reaction rate is reduced to cause disproportionation reaction of DHDCPD at the same time and that DCPD formed by the above disproportionation reaction is carbonylated and esterified, so that an ester having an unsaturated bond is formed.

It has been found from the above knowledge that a satisfactory acid strength can be maintained by separating a carbonylation step from an esterification step, whereby carbonylation can quickly be promoted, so that a disproportionation product can be inhibited and that as a result thereof, an amount of a formed impurity ester having an unsaturated bond can be reduced.

Also, it has been found that an Endo/Exo isomer ratio of the product is determined in carbonylation reaction and that it is an important requisite for obtaining TCDCE having a structural ratio of 1.0 or more in an Endo isomer/Exo isomer at a high yield to carry out reaction conditions in optimum ranges in the above carbonylation reaction.

Further, it has been found that TCDCE having an Endo/Exo isomer ratio of 1.0 or more in an Endo isomer/Exo isomer ratio is effectively obtained by adding separately an isomerization step between a carbonylation step and an esterification step.

In addition thereto, it has been found that an impurity aldehyde is changed to an acetal compound having a higher boiling point than that of TCDCE by adding an acid catalyst and specific alcohol to a TCDE crude product and treating them under heating and that the resulting acetal compound can be separated by a simple distilling operation.

The present invention has been completed based on the knowledges described above.

That is, the present invention provides:

(1) a process for producing tricyclo[5.2.1.0$^{2,6}$]decane-2-carboxylic acid ester by reacting tricyclo[5.2.1.0$^{2,6}$]deca-3-ene with carbon monoxide and alcohol in the presence of HF, wherein carried out separately are (a) a step in which tricyclo[5.2.1.0$^{2,6}$]deca-3-ene is reacted with carbon monoxide to produce acyl fluoride and (b) a step in which acyl fluoride obtained in the step described above is reacted with alcohol to produce an ester, (2) the process as described in the above item (1), wherein the step (a) is carried out on the conditions of an HF/tricyclo[5.2.1.0$^{2,6}$]deca-3-ene ratio of 3 to 25 and a reaction temperature of 40 to 90° C., and then the step (b) is carried out, whereby produced is tricyclo[5.2.1.0$^{2,6}$]decane-2-carboxylic acid ester in which a structural ratio of exo-tricyclo[5.2.1.0$^{2,6}$]decane-endo-2-carboxylic acid ester/endo-tricyclo[5.2.1.0$^{2,6}$]decane-exo-2-carboxylic acid ester is 1.0 or more, (3) a process for producing tricyclo[5.2.1.0$^{2,6}$]decane-2-carboxylic acid ester in which a structural ratio of exo-tricyclo[5.2.1.0$^{2,6}$]decane-endo-2-carboxylic acid ester/endo-tricyclo[5.2.1.0$^{2,6}$]decane-exo-2-carboxylic acid ester is 1.0 or more by reacting tricyclo[5.2.1.0$^{2,6}$]deca- 3-ene with carbon monoxide and alcohol in the presence of HF, wherein carried out are (a-1) a step in which tricyclo[5.2.1.0$^{2,6}$]deca-3-ene is reacted with carbon monoxide in the presence of HF on the condition of a reaction temperature of 20° C. or higher and lower than 40° C. to produce tricyclo[5.2.1.0$^{2,6}$]decane-2-carboxylic fluoride, (a-2) a step in which an HF solution of tricyclo[5.2.1.0$^{2,6}$]decane-2-carboxylic fluoride obtained in the step (a-1) described above is held on the condition of 40 to 70° C. to thereby carry out an isomerizing reaction and (b-1) a step in which tricyclo[5.2.1.0$^{2,6}$]decane-2-carboxylic fluoride obtained after isomerization in the step (a-2) described above is reacted with alcohol to produce an ester, (4) the process as described in the above item (3), wherein the step (a-1) is carried out on the condition of an HF/tricyclo[5.2.1.0$^{2,6}$]deca-3-ene ratio of 4 to 12, (5) the process as described in the above item (3) or (4), wherein the step (a-2) is carried out under elevated pressure of carbon monoxide at 1 to 3 MPa, (6) a process for producing ethyl tricyclo[5.2.1.0$^{2,6}$]decane-2-carboxylate by reacting tricyclo[5.2.1.0$^{2,6}$]deca-3-ene with carbon monoxide and ethanol in the presence of HF, wherein a crude product of ethyl tricyclo[5.2.1.0$^{2,6}$]decane-2-carboxylate is subjected to contact treatment with glycol represented by Formula (I) in the presence of an acid catalyst:

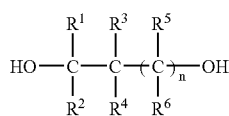

(I)

(wherein R$^1$ to R$^6$ each represent a hydrogen atom, methyl or ethyl, and they may be the same as or different from each other; and n represents 0 or 1), and then it is distilled, and (7) the process as described in the above item (6), wherein in subjecting the crude product of ethyl tricyclo[5.2.1.0$^{2,6}$]decane-2-carboxylate to the contact treatment with the glycol described above in the presence of the acid catalyst, the above contact treatment is carried out at a temperature falling in a range of 100 to 180° C.

If tricyclo[5.2.1.0$^{2,6}$]decane-2-carboxylic acid ester is produced by the process of the present invention, an ester having an unsaturated bond which is difficult to be separated from the product can be inhibited from being by-produced, and therefore hydrogenating treatment which has so far been required can be omitted.

Also, selection of conditions for carbonylation or addition of an isomerization step between a carbonylation step and an esterification step makes it possible to obtain a product which is particularly useful as a perfume or a perfume component and which has an Endo/Exo isomer ratio of 1.0 or more at a high yield, and therefore the process of the above embodiment in the present invention is industrially very advantageous.

Further, according to the preferred refining process in the present invention, subjecting a TCDE crude product to specific treatment makes it possible to effectively remove impurity aldehyde by ordinary distilling treatment without using a distilling column having a high separation efficiency and makes it possible to industrially advantageously produce high purity TCDE which is suited as a perfume or a perfume component.

BEST MODE FOR CARRYING OUT THE INVENTION

In the process of the present invention, tricyclo[5.2.1.0$^{2,6}$]deca-3-ene (DHDCPD) which is used as a raw material shall not specifically be restricted in an origin thereof, and it may be obtained by any method. Usually, it is prepared by hydrogenating DCPD by an ordinary method.

In the process of the present invention, carried out separately are (a) a step in which DHDCPD described above is used as a raw material to produce acyl fluoride by carbonylation reaction and (b) a step in which an ester is produce from acyl fluoride obtained in the step (a) described above.

The carbonylation reaction of DHDCPD in the step (a) described above is carried out under pressurizing carbon monoxide in the presence of an HF catalyst. In this case, inert gas such as nitrogen and methane may be contained in carbon monoxide. A partial pressure of carbon monoxide shall not specifically be restricted and is usually 0.5 to 5 MPa. If a partial pressure of carbon monoxide falls in the range described above, the carbonylation reaction proceeds sufficiently, and side reactions such as disproportionation and polymerization are inhibited. In addition thereto, an unsaturated compound is inhibited from being mixed in the product TCDCE, and a so large amount of a facility cost is not required. The preferred partial pressure of carbon monoxide falls in a range of 1 to 3 MPa.

In the above case, substantially anhydrous HF is preferably used as the HF catalyst. A use amount of HF is selected in a range of usually 3 to 25 times mole, preferably 5 to 15 times mole based on raw material DHDCPD from the view points of a satisfactory advance in the carbonylation reaction, an inhibition in side reactions such as disproportionation and polymerization, an inhibition in mixing of an unsaturated compound in the product TCDCE, a separating cost of HF and an apparatus volume efficiency.

The type of the reaction shall not specifically be restricted and may be any of a semi-continuous type, a continuous type and the like.

In the process of the present invention, a reaction temperature in the carbonylation is particularly important for obtaining TCDEC having an Endo isomer/Exo isomer ratio of 1.0 or more at a high yield.

Carbonylation reaction using an HF catalyst is carried out usually in the vicinity of −30 to 20° C. in many cases, and therefore an influence exerted on an isomer structural ratio by a reaction temperature falling in the above range has been investigated in details. As a result thereof, it has been found that a higher Endo isomer/Exo isomer ratio is given at a lower temperature and that a low temperature condition of −20° C. or lower is required for obtaining TCDEC having an Endo isomer/Exo isomer ratio falling in the vicinity of 1.0. However, it has become clear that a reaction yield in the carbonylation is notably low on the above condition to by-produce a large amount of products having a high boiling point and that it is a method which is difficult to industrially carry out.

Then, intensive investigations have been repeated to obtain the unexpected results that acyl fluoride having an Endo isomer/Exo isomer ratio of 1.0 or more is obtained very easily on a high temperature condition of 40° C. or higher and that the higher Endo isomer/Exo isomer ratio is given on a higher temperature condition. Further, it has been found that in the above condition range, acyl fluoride is obtained at a higher yield as compared with that on the low temperature condition described above.

That is, it is advantageous in the present invention to carry out carbonylation reaction at a temperature falling in a range of 40 to 90° C. The carbonylation reaction carried out at a temperature falling in the above range makes it possible to obtain acyl fluoride having an Endo isomer/Exo isomer ratio of 1.0 or more and makes it possible to inhibit side reactions such as polymerization. The preferred reaction temperature is selected in a range of 40 to 70° C.

In the present invention, there may be used a reaction solvent which has an ability to dissolve raw material DHDCPD and which is inert to DHDCPD and HF, for example, saturated aliphatic hydrocarbons such as hexane, heptane, decane and the like. In this case, the polymerization reaction is further inhibited, and the yield is elevated. However, use of a large amount of the solvent brings about a reduction in a volume efficiency of the reaction and a deterioration in the energy consumption rate required for separation, and therefore use or non-use thereof and the use amount are suitably selected.

Thus, acyl fluoride formed by the carbonylation reaction is reacted with alcohol at the subsequent step (b) to be introduced into TCDCE.

In this case, acyl fluoride may be once separated and esterified with alcohol in the second presence of the HF catalyst, but usually taken is a method in which the carbonylation reaction solution containing the HF catalyst is reacted with alcohol as it is to produce TCDCE. In this case, a prescribed amount of the alcohol is preferably added to the carbonylation reaction solution, and in a method in which the carbonylation reaction solution is added to the alcohol, the risk of forming water is high since HF is coexistent in excess alcohol. If water is formed in the system, corrosiveness is notably increased to bring about troubles on the process.

Lower alcohols having 1, 2 or 3 carbon atoms, that is, methanol, ethanol, n-propanol and isopropanol are preferably used as the alcohol used at the above step (b).

The above esterification reaction is carried out at a temperature falling in a range of usually 20° C. or lower, preferably −20 to 10° C. from the view points of an inhibition in decomposition of the ester formed and an inhibition in by-production of water by dehydration reaction of alcohol added.

HF is distilled off from the esterified product thus obtained, and then it is refined by a conventional method such as distillation, whereby high purity TCDCE having a small content of an unsaturated compound can be obtained. Further, selection of the reaction conditions makes it possible to obtain TCDCE having an Endo isomer/Exo isomer ratio of 1.0 or more.

The present invention provides a method in which an isomerization step is added between the carbonylation step and the esterification step as another method for obtaining TCDCE having an Endo isomer/Exo isomer ratio of 1.0 or more at a high yield and a good productivity.

In order to obtain TCDCE having an Endo isomer/Exo isomer ratio of 1.0 or more, tricyclo[5.2.1.0$^{2,6}$]decane-2-carboxylic fluoride (hereinafter referred to as TCD-COF) having an Endo isomer/Exo isomer ratio of 1.0 or more has to be formed immediately after DHDCPD is carbonylated. In the above another method, the isomerization step is carried out after the carbonylation step, and therefore an Endo isomer/Exo isomer ratio of TCD-COF formed at the carbonylation step does not have to be considered, so that it becomes possible to select the optimum conditions in terms of the yield and the productivity.

In respect to the carbonylation step, attentions have been paid only to the yield to investigate a relation thereof with the reaction temperature, and it has become clear that the condition of the high yield is present in the vicinity of 30° C.

Accordingly, the carbonylation step (a-1) in another method is carried out in a range of 20° C. or higher and lower than 40° C., preferably 25 to 35° C. The other reaction conditions in the carbonylation step (a-1) are the same as in the step (a) described above. A use amount of HF is selected in a range of usually 4 to 12 times mole, preferably 6 to 10 times mole based on raw material DHDCPD.

TCD-COF formed in the carbonylation reaction at the above step (a-1) continues to be isomerized at the isomerizing step (a-2) so that an Endo isomer/Exo isomer ratio of 1.0 or more is obtained. In this case, the isomerizing step may be carried out in the second presence of the HF catalyst after once separating TCD-COF, but usually the reaction solution obtained in the carbonylation reaction is subjected to isomerization reaction as it is without separating TCD-COF. The isomerization reaction is carried out as well under pressurizing by carbon monoxide. In this case, a partial pressure of carbon monoxide is selected in a range of usually 0.5 to 5 MPa, preferably 1 to 3 MPa in terms of an inhibition in the decomposition of TCD-COF and the apparatus.

A reaction temperature in the isomerization reaction is selected in a range of 40 to 70° C., preferably 40 to 65° C. considering the reaction rate, an inhibition in the decomposition of TCD-COF and an inhibition in the isomerization to the other isomers.

TCD-COF which is controlled in an Endo isomer/Exo isomer ratio in the above isomerizing step (a-2) continues to be reacted with alcohol at the esterifying step (b-1), whereby TCDCE is prepared. In this case, TCD-COF may be subjected to the esterification reaction with alcohol again under the presence of the HF catalyst after once separating TCD-COF, but usually taken is a method in which the isomerization reaction solution is reacted with alcohol as it is without separating TCD-COF to produce TCDCE. In this case, a prescribed amount of alcohol is preferably added to the isomerization reaction solution, and in a method in which the isomerization reaction solution is added to alcohol, the risk of forming water is high since HF is coexistent in excess alcohol. If water is formed in the system, corrosiveness is notably increased to bring about troubles on the process.

Lower alcohols having 1, 2 or 3 carbon atoms, that is, methanol, ethanol, n-propanol and isopropanol are preferably used as the alcohol used in the present invention.

The above esterification reaction is carried out at a temperature falling in a range of usually 20° C. or lower, preferably −20 to 10° C. from the view points of an inhibition in the decomposition of the ester formed and an inhibition in the by-production of water by dehydration reaction of alcohol added.

HF is distilled off from the esterified product thus obtained, and then it is refined by a conventional method such as distillation, whereby high purity TCDCE having an Endo isomer/Exo isomer ratio of 1.0 or more can be obtained.

The TCDE crude product obtained in the present invention is subjected to contact treatment with glycol and then distilled in the presence of an acid catalyst, whereby refined TCDE from which impurity aldehyde is removed can be produced. Resulting crude ester can be subjected to contact treatment with glycol in the presence of the acid catalyst, but it may be treated after removing low boiling matters and high boiling matters by a simple distilling operation.

In general, a process for producing refined TCDE described above can usually be applied to a process in which DHDCPD is reacted with carbon monoxide and alcohol in the presence of HF to produce TCDE.

The acid catalyst described above includes liquid acids such as sulfuric acid and solid acids such as activated clay, acid clay, hojacite, X type zeolite, Y type zeolite, mordenite, silica alumina and strong acid ion exchange resins. They may be used alone or in combination of two or more kinds thereof. An addition amount of the above acid catalyst shall not specifically be restricted and falls usually in a range of 0.1 to 10.0 mass % based on the TCDE crude product. Addition of 0.1 mass % or more of the above acid catalyst makes it possible to sufficiently reduce impurity aldehyde and makes it possible to control a content of the impurity aldehyde contained in the product to 0.5 mass % or less only by a simple distilling operation. An addition amount of the acid catalyst is advantageously 10.0 mass % or less in terms of a cost for separating TCDE from the acid catalyst. A preferred addition amount of the above acid catalyst falls in a range of 0.5 to 5.0 mass %.

On the other hand, glycol represented by Formula (I) can be used as the glycol:

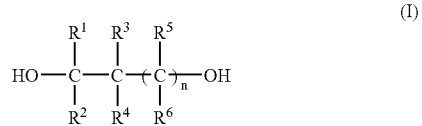

(I)

In Formula (I) described above, $R^1$ to $R^6$ each represent a hydrogen atom, methyl or ethyl, and they may be the same as or different from each other; and n represents 0 or 1.

Use of the glycol represented by Formula (I) makes it possible to allow acetalization of impurity aldehyde to sufficiently proceed to remove the above impurity aldehyde by a simple distilling operation. For example, ethylene glycol, triethylene glycol, propylene glycol and neopentyl glycol can be given as the glycol represented by Formula (I). They may be used alone or in combination of two or more kinds thereof.

An addition amount of the glycol described above is selected in a range of usually 0.1 to 10.0 mass %, preferably 0.5 to 5.0 mass % based on the TCDE crude product. The contact treatment temperature falls preferably in a range of 80 to 200° C., particularly preferably 100 to 180° C. considering the reaction rate, a distillation loss of the glycol added and a distillation loss of the product. The treating time is sufficiently 1 to 5 hours.

A reaction for converting impurity aldehyde to an acetal compound is an equilibrium reaction, and therefore the reaction can be promoted by removing water formed to the outside of the system. A means for removing water includes a method in which water is accompanied by flowing gas inert to the TCDE crude product, for example, nitrogen, a method in which added is a dehydrating agent which is not reacted with the TCDE crude product, for example, anhydrous sodium sulfate and a method in which a solvent immiscible with water and having an adequate boiling point is added and in which water is removed under refluxing of the above solvent.

After the treatment, the acid catalyst is removed by neutralization, washing with water or filtering, and then the TCDE crude product is refined by distillation, whereby TCDE of the product is obtained.

EXAMPLES

Next, the present invention shall be explained in further details with reference to examples, but the present invention shall by no means be restricted by these examples.

Preparation Example 1

High purity DCPD which was commercially available was reacted at a hydrogen pressure of 2 MPa and a reaction temperature of 90° C. for about 5 hours in the presence of a Cu—Cr hydrogenating catalyst until hydrogen was not observed to be absorbed. The Cu—Cr hydrogenating catalyst was removed from the reaction solution by filtering, and then it was refined by distillation to obtain DHDCPD which was a raw material (purity: 98.5%).

Example 1

A stainless steel-made autoclave having a content volume of 500 ml which was equipped with a knuck drive type stirrer, three inlet nozzles at an upper part and a drawing nozzle at a bottom and in which an internal temperature could be controlled by means of a jacket was used to carry out an experiment.

First, the autoclave was substituted in an inside thereof with carbon monoxide, and then 150 g (7.5 mole) of hydrogen fluoride was introduced thereinto and cooled down to 0° C., followed by pressurizing up to 2 MPa by carbon monoxide. The autoclave was fed from an upper pat thereof with 12.6 g of a n-heptane solution dissolving 101 g (0.75 mole) of DHDCPD while maintaining a reaction temperature at 0° C. and a reaction pressure at 2 MPa to synthesize acyl fluoride by carbonylation. After finishing feeding DHDCPD, stirring was continued for about 10 minutes until carbon monoxide was not observed to be absorbed. In this case, an absorbing amount of carbon monoxide was 0.39 mole.

Next, the autoclave was fed from an upper pat thereof with 34.5 g (7.5 mole) of ethanol to carry out esterification for one hour under stirring.

The reaction solution was drawn from the bottom of the autoclave into ice and water to separate an oil phase from an aqueous phase, and then the oil phase was washed twice with 100 ml of a 2 mass % sodium hydroxide aqueous solution and twice with 100 ml of distilled water and dehydrated on 10 g of anhydrous sodium sulfate. The liquid thus obtained was analyzed by gas chromatography according to an internal standard method. As a result thereof, obtained were the reaction results of a TCDCE yield of 51.2% (based on DHDCPD) and an Endo isomer/Exo isomer ratio of 0.69, and 0.5 mass % of an unsaturated compound was contained.

Comparative Example 1

A raw material solution having a composition of DHDCPD/ethanol/n-heptane=1/0.7/0.75 (mass ratio) (mole ratio=1/2/0.3) was used to carry out carbonylation and esterification at the same time at a reaction temperature of 0° C. and a carbon monoxide pressure of 2 MPa. The resulting sample was pretreated in the same manner as in Example 1 and analyzed to find that obtained were the reaction results of a TCDCE yield of 43.5% (based on DHDCPD) and an Endo isomer/Exo isomer ratio of 0.70 and that 5.80 mass % of the unsaturated compound was contained. The unsaturated compound was notably formed as compared with that in Example 1.

Example 2

The same operation as in Example 1 was carried out, except that in Example 1, the temperature of carbonylation was changed from 0° C. to 45° C.

As a result thereof, obtained were the reaction results of a TCDCE yield of 51.0% and an Endo isomer/Exo isomer ratio of 1.56, and 0.01 mass % of the unsaturated compound was contained.

Comparative Example 2

The same operation as in Comparative Example 1 was carried out, except that in Comparative Example 1, the temperature of carbonylation was changed from 0° C. to 45° C.

As a result thereof, obtained were the reaction results of a TCDCE yield of 50.1% and an Endo isomer/Exo isomer ratio of 0.59, and 0.61 mass % of the unsaturated compound was contained.

In above Comparative Example 2, almost the same yield as in Example 2 was obtained, but the Endo isomer/Exo isomer ratio was 0.59 and far low as compared with that in Example 2.

Example 3

The same operation as in Example 1 was carried out, except that in Example 1, the temperature of carbonylation was changed from 0° C. to 40° C.

As a result thereof, obtained were the reaction results of a TCDCE yield of 54.5% and an Endo isomer/Exo isomer ratio of 1.22, and 0.00 mass % of the unsaturated compound was contained.

Example 4

The same operation as in Example 1 was carried out, except that in Example 1, the temperature of carbonylation was changed from 0° C. to −25° C.

As a result thereof, obtained were the reaction results of a TCDCE yield of 35.0% and an Endo isomer/Exo isomer ratio of 1.22, and 2.6 mass % of the unsaturated compound was contained.

Example 5

The same operation as in Example 1 was carried out, except that in Example 1, the temperature of carbonylation was changed from 0° C. to 70° C.

As a result thereof, obtained were the reaction results of a TCDCE yield of 35.0% and an Endo isomer/Exo isomer ratio of 10.10, and 0.02 mass % of the unsaturated compound was contained.

Example 6

The same operation as in Example 1 was carried out, except that in Example 1, a temperature of carbonylation was changed from 0° C. to 100° C.

As a result thereof, obtained were the reaction results of a TCDCE yield of 20.0% and an Endo isomer/Exo isomer ratio of 24.00, and 0.02 mass % of the unsaturated compound was contained.

Example 7

The same operation as in Example 1 was carried out, except that in Example 1, changed were the HF/DHDCPD mole ratio to 5, the carbon monoxide partial pressure to 4 MPa and the temperature to 70° C. in carbonylation.

As a result thereof, obtained were the reaction results of a TCDCE yield of 40.0% and an Endo isomer/Exo isomer ratio of 1.86, and 0.02 mass % of the unsaturated compound was contained.

Example 8

The same operation as in Example 7 was carried out, except that in Example 7, the HF/DHDCPD mole ratio was reduced to 2.5 in carbonylation.

As a result thereof, obtained were the reaction results of a TCDCE yield of 30.0% and an Endo isomer/Exo isomer ratio of 1.85, and 0.01 mass % of the unsaturated compound was contained.

Example 9

A stainless steel-made autoclave having a content volume of 500 ml which was equipped with a knuck drive type stirrer, three inlet nozzles at an upper part and a drawing nozzle at a bottom and which could control an internal temperature by means of a jacket was used to carry out an experiment.

First, the autoclave was substituted in an inside thereof with carbon monoxide, and then 128 g (6.4 mole) of hydrogen fluoride was introduced thereinto, and after controlling the liquid temperature to 30° C., the autoclave was pressurized up to 2 MPa by carbon monoxide.

The autoclave was charged from an upper pat thereof with 207 g of a n-heptane solution dissolving 107.7 g (0.80 mole) of DHDCPD while maintaining a reaction temperature at 30° C. and a reaction pressure at 2 MPa to carry out carbonylation reaction. After finishing feeding DHDCPD, stirring was continued for about 10 minutes until carbon monoxide was not observed to be absorbed.

A part of the reaction solution thus obtained was sampled into cooled ethanol, and water was added to separate an oil phase from an aqueous phase. The oil phase was neutralized ands washed with water, and the resulting oil phase was analyzed by gas chromatography to find that an Endo isomer/Exo isomer ratio was 0.53.

Then, the reaction solution temperature was raised up to 45° C. while maintaining the reaction pressure at 2 MPa, and this temperature was maintained for 3 hours to carry out isomerization reaction. After maintaining for 3 hours, the reaction solution temperature was cooled down to −10° C., and the autoclave was fed from an upper part thereof with 36.9 g (0.80 mole) of ethanol to carry out esterification for one hour under stirring.

The reaction solution was drawn from the bottom of the autoclave into ice and water to separate an oil phase from an aqueous phase, and then the oil phase was washed twice with 100 ml of a 2 mass % sodium hydroxide aqueous solution and twice with 100 ml of distilled water and dehydrated on 10 g of anhydrous sodium sulfate. The liquid thus obtained was analyzed by gas chromatography according to an internal standard method. As a result thereof, obtained were the reaction results of a TCDCE yield of 57.2% (based on DHDCPD) and an Endo isomer/Exo isomer ratio of 1.29.

Example 10

The same operation as in Example 9 was carried out, except that the isomerization reaction was carried out at a pressure of 0.3 MPa. The resulting oil phase was analyzed to find that obtained were the reaction results of a TCDCE yield of 53.0% (based on DHDCPD) and an Endo isomer/Exo isomer ratio of 1.30.

Example 11

The same operation as in Example 9 was carried out, except that a use amount of HF was changed to 96.0 g (4.8 mole). The resulting oil phase was analyzed to find that obtained were the reaction results of a TCDCE yield of 55.7% (based on DHDCPD) and an Endo isomer/Exo isomer ratio of 1.20.

A use amount of hydrogen fluoride was reduced, but the high yield was obtained.

Example 12

A stainless steel-made autoclave having a content volume of 500 ml which was equipped with a knuck drive type stirrer, three inlet nozzles at an upper part and a drawing nozzle at a bottom and in which an internal temperature could be controlled by means of a jacket was substituted with carbon monoxide. Then, 3 kg (150 mole) of hydrogen fluoride was introduced thereinto, and the autoclave was pressurized up to 2 MPa by carbon monoxide.

The autoclave was fed from an upper pat thereof with 2950 g of a raw material liquid having a composition of DHDCPD/n-heptane=1/0.75 (mass ratio) while maintaining a reaction temperature at 40° C. and a reaction pressure at 2 MPa to carry out carbonylation. After finishing feeding the raw material, a temperature of the reaction solution was lowered to 0° C., and the pressure was reduced down to an atmospheric pressure. Then, 575 g of ethanol was fed to carry out esterification reaction. Further, after stirring was continued for one hour, hydrogen fluoride which was the catalyst was removed by distillation, and the resulting reaction solution was neutralized with a 2 mass % NaOH aqueous solution and washed with water. Then, it was rectified by means of a distilling column having a theoretical plate number of 5 plates to obtain a TCDE crude product. This TCDE crude product had a purity 97.01 mass % and contained 1.14 mass % of impurity aldehyde.

Next, a four neck flask of 2 liter equipped with a mechanical stirrer, a nitrogen-introducing nozzle, a thermometer and a an exhaust gas line was charged with 500 g of the TCDE crude product described above, 10 g of activated clay and 10 g of ethylene glycol, and the solution was heated and stirred at 150° C. under nitrogen flow. The same condition was maintained for 3 hours, and then the solution was cooled down to a room temperature. After cooling down, the activated clay was filtered off, and the resulting liquid was analyzed by gas chromatography (GC) to find that the liquid had a TCDE purity of 96.40 mass % and an impurity aldehyde content of 0.44 mass % and confirm that in addition thereto, 0.89 mass % of an acetal compound of impurity aldehyde and ethylene glycol was formed.

The liquid 400 g out of the liquid obtained by filtering the activated clay was rectified by means of a rectifying column having a theoretical plate number of 20 plates to obtain a compound having a TCDE purity of 99.58 mass % and an impurity aldehyde content of 0.42 mass % as a main distillate. The above compound had a sweet fruit-like fragrance and was of an excellent fragrant characteristic as a fragrant composition.

Example 13

The same operation as in Example 12 was carried out, except that the treating temperature was changed to 110° C. A liquid obtained by filtering the activated clay was subjected to GC analysis to find that the liquid had a TCDE purity of 96.30 mass % and an impurity aldehyde content of 0.48 mass % and confirm that in addition thereto, 0.78 mass % of an acetal compound of impurity aldehyde and ethylene glycol was formed.

Example 14

The same operation as in Example 12 was carried out, except that ethylene glycol was changed to trimethylene glycol. A liquid obtained by filtering the activated clay was subjected to GC analysis to find that the liquid had a TCDE purity of 96.35 mass % and an impurity aldehyde content of 0.49 mass % and confirm that in addition thereto, 0.73 mass % of an acetal compound of impurity aldehyde and trimethylene glycol was formed.

INDUSTRIAL APPLICABILITY

According to the present invention, TCDE having a small content of an unsaturated compound and an Endo isomer/Exo isomer ratio of 1.0 or more can efficiently be obtained by selecting the reaction conditions or adding an isomerizing step between a carbonylizing step and an esterifying step. TCDE having the above properties has an excellent fragrance and is very useful as a perfume or a perfume component.

Further, according to the preferred refining process in the present invention, high purity TCDE in which impurity aldehyde is reduced and which is further excellent in a fragrance can industrially advantageously be obtained.

What is claimed is:

1. A process for producing tricyclo[$5.2.1.0^{2,6}$]decane-2-carboxylic acid ester by reacting tricyclo[$5.2.1.0^{2,6}$]deca-3-ene with carbon monoxide and alcohol in the presence of HF, the process comprising (a) a step of reacting tricyclo[$5.2.1.0^{2,6}$]deca-3-ene with carbon monoxide until carbon monoxide is no longer absorbed by the reaction system, to produce acyl fluoride, wherein the step (a) is carried out in the absence of alcohol, and thereafter (b) a step of adding the alcohol to the reaction system and a step of reacting the acyl fluoride produced in the step (a) with the alcohol to produce the ester.

2. The process as described in claim 1, wherein the step (a) is carried out under the conditions of an HF/tricyclo[$5.2.1.0^{2,6}$]deca-3-ene ratio of 3 to 25 and a reaction temperature of 40 to 90° C., and then the step (b) is carried out, whereby produced is tricyclo[$5.2.1.0^{2,6}$]decane-2-carboxylic acid ester in which a structural ratio of exo-tricyclo[$5.2.1.0^{2,6}$]decane-endo-2-carboxylic acid ester/endo-tricyclo[$5.2.1.0^{2,6}$]decane-endo-2-carboxylic acid ester is 1.0 or more.

3. A process for producing tricyclo[$5.2.1.0^{2,6}$]decane-2-carboxylic acid ester having a ratio of exo-tricyclo[$5.2.1.0^{2,6}$]decane-endo-2-carboxylic acid ester/endo-tricyclo[$5.2.1.0^{2,6}$]decane-exo-2-carboxylic acid ester of 1.0 or more, which comprises (a-1) a step of reacting tricyclo[$5.2.1.0^{2,6}$]deca-3-ene with carbon monoxide in the presence of HF at a reaction temperature of 20° C. or higher and lower than 40° C. until carbon monoxide is no longer absorbed by the reaction system, to produce an HF solution containing tricyclo[5.2.1.0$^{2,6}$]decane-2-carboxylic fluoride including exo-tricyclo[5.2.1.0$^{2,6}$]decane-endo-2-carboxylic fluoride and endo-tricyclo[5.2.1.0$^{2,6}$]decane-exo-2-carboxylic fluoride, wherein the step (a-1) is carried out in the absence of alcohol, (a-2) a step in which the HF solution is held at 40 to 70° C., thereby isomerizing endo-tricyclo[5.2.1.0$^{2,6}$]decane-exo-2-carboxylic fluoride into exo-tricyclo[5.2.1.0$^{2,6}$]decane-endo-carboxylic fluoride, and thereafter (b-1) a step of adding the alcohol to the reaction system and a step in which tricyclo[5.2.1.0$^{2,6}$]decane-2-carboxylic fluoride obtained after isomerization in the step (a-2) is reacted with the alcohol to produce the ester.

4. The process as described in claim 3, wherein the step (a-1) is carried out under the condition of an HF/tricyclo[5.2.1.0$^{2,6}$]deca-3-ene ratio of 4 to 12.

5. The process as described in claim 4, wherein the step (a-2) is carried out under pressurizing of carbon monoxide at 1 to 3 MPa.

6. A process for producing ethyl tricyclo[5.2.1.0$^{2,6}$]decane-2-carboxylate by reacting tricyclo[5.2.1.0$^{2,6}$]deca-3-ene with carbon monoxide and ethanol in the presence of HF, wherein a crude product of ethyl tricyclo[5.2.1.0$^{2,6}$]decane-2-carboxylate is subjected to contact treatment with glycol represented by Formula (I) in the presence of an acid catalyst:

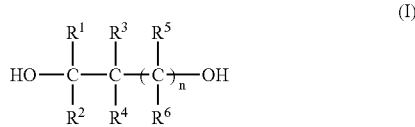

(I)

(wherein $R^1$ to $R^6$ each represent a hydrogen atom, methyl or ethyl, and they may be the same as or different from each other; and n represents 0 or 1), and then impurities are removed by distillation.

7. The process as described in claim 6, wherein in subjecting the crude product of ethyl tricyclo[5.2.1.0$^{2,6}$]decane-2-carboxylate to the contact treatment with the glycol described above in the presence of the acid catalyst, the above contact treatment is carried out at a temperature falling in a range of 100 to 180° C.

8. The process as described in claim 3, wherein the step (a-2) is carried out under pressurizing of carbon monoxide at 1 to 3 MPa.

9. The process as described in claim 1, wherein the step (a) of reacting tricyclo[5.2.1.0$^{2,6}$]deca-3-ene with carbon monoxide is performed at a temperature in the range of 40 to 90° C.

10. The process as described in claim 1, wherein the step (a) of reacting tricyclo[5.2.1.0$^{2,6}$]deca-3-ene with carbon monoxide is performed in a reaction solvent for the tricyclo[5.2.1.0$^{2,6}$]deca-3-ene.

11. The process as described in claim 1, wherein said alcohol is an alcohol having 1, 2 or 3 carbon atoms.

12. The process as described in claim 9, wherein the step (b) of reacting the acyl fluoride with the alcohol is performed at a temperature in the range of −2 to 10° C.

13. The process as described in claim 3, wherein the step (a-2) in which the HF solution is held at 40 to 70° C. is performed under a partial pressure of carbon monoxide of 0.5 to 5 MPa.

14. The process as described in claim 6, wherein the glycol is included in an amount of 0.1 to 10.0 mass %, based on the crude product.

* * * * *